United States Patent [19]

O'Lenick, Jr. et al.

[11] Patent Number: 5,237,035
[45] Date of Patent: Aug. 17, 1993

[54] SILICONE PHOSPHOLIPID POLYMERS

[75] Inventors: Anthony J. O'Lenick, Jr., Lilburn; Jeff K. Parkinson, Lawrenceville, both of Ga.

[73] Assignee: Siltech Corp., Toronto, Canada

[21] Appl. No.: 997,036

[22] Filed: Dec. 28, 1992

[51] Int. Cl.$^5$ .................. C08G 77/06; C08G 77/30
[52] U.S. Cl. .................................. 528/27; 528/30; 528/28; 528/33; 525/474; 525/538
[58] Field of Search .............. 528/30, 27, 28, 33; 525/474, 538; 556/450

[56] References Cited

U.S. PATENT DOCUMENTS

| | | | |
|---|---|---|---|
| 4,215,064 | 7/1980 | Lindemann et al. | 260/403 |
| 5,070,171 | 12/1991 | O'Lenick, Jr. | 528/33 |
| 5,091,493 | 2/1992 | O'Lenick, Jr. | 528/30 |
| 5,093,452 | 3/1992 | O'Lenick, Jr. | 528/25 |
| 5,149,765 | 8/1992 | O'Lenick, Jr. | 528/25 |

*Primary Examiner*—John C. Bleutge
*Assistant Examiner*—Margaret Glass

[57] ABSTRACT

The present invention relates to a series of novel silicone phospholipid polymers which are highly lubricious, produce high levels of copious foam, have low irritation properties and are film formers when applied to hair and skin. The compounds, because they are based upon terminal dimethicone copoylols make flat polymers when phosphated and derivatized. As will become apparent, the polymers of the present invention will orientate themselves into planar sheets, silicone on one side of the plane, fatty portion on the other side in aqueous and other solutions. These flat polymers have the unexpected property of producing non-occlusive films when applied to hair skin and fiber.

13 Claims, No Drawings

SILICONE PHOSPHOLIPID POLYMERS

BACKGROUND OF THE INVENTION (1) Field of Invention

The present invention relates to a series of novel silicone phospholipid polymers which are highly lubricious, produce high levels of copious foam, have low irritation properties and are film formers when applied to hair and skin. The compounds, because they are based upon terminal dimethicone copoylols make flat polymers when phosphated and derivatized. As will become apparent, the polymers of the present invention will orientate themselves into planar sheets, silicone on one side of the plane, fatty portion on the other side in aqueous and other solutions. These flat polymers have the unexpected property of producing non-occlusive films when applied to hair skin and fiber. They contain a pendant ionizable phosphate group and a quaternary amine compound are amphoterics that is they contain both a positive and negative charge in the same molecule. They resemble polymers of naturally occurring phospholipids and tend to form bilayer sheets rather than micelles when used in making oil in water emulsions. Since the compounds of the present invention are high molecular weight silicone polymers, they have a high degree of oxidative stability, even at elevated temperatures and are nonirritating to skin and eyes. In addition, these compounds are non volatile and exhibit a inverse cloud point. These combination of properties makes these polymers ideally suited for use in personal care applications.

The technology used to produce the polymeric phospholipids of the present invention is very flexible and allows us to prepare performance tailored molecules for specific applications. As will become obvious, these materials unlike phosphobetaines, form lipid bilayers in aqueous solution and consequently are called phospholipids rather than phosphobetaines. This property is based upon the specific polymeric structure as will become apparent.

(2) Description of the Arts and Practices

Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commericial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not ionically bonded the effect is very transient. The product is removed with one washing.

Fatty Phosphobetaines have been known since 1974. There are several patents which have issued on this topic.

U.S. Pat. Nos. 3,856,893 and 3,928,509 both issued to Diery disclose the basic technology used to make phosphobetaines and the alkyl derivatives.

Later, phosphobetaines based upon alkylamidoamines and imidazolines rather than alkyl amines were patented in U.S. Pat. No. 4,209,449 issued in 1980 to Mayhew and O'Lenick. This patent teaches that phosphate quats can be prepared by the reaction of a phosphate salt, three equivalents of epichlorohydrin and in a subsequent step, three equivalents of a tertiary amine.

U.S. Pat. No. 4,215,064 issued in 1980 to Lindemann et al teaches the basic technology that is used for the preparation of amido and imidazoline based phosphobetaines. These compounds can be prepared by the reaction of a phosphate salt, one equivalent of epichlorohydrin and one equivalent of a tertiary amine.

U.S. Pat. No. 4,243,602 issued in 1981 to O'Lenick and Mayhew teaches the basic technology that is used for the preparation of phosphobetaines based upon phosphorous acid salts. These compounds can be prepared by the reaction of a phosphorous acid salt, one equivalent of epichlorohydrin and one equivalent of a tertiary amine.

U.S. Pat. No. 4,261,911 issued in 1981 to Lindemann et al teaches the utilization of phosphobetaines based upon phosphorous acid. These compounds are useful as surfactants.

U.S. Pat. No. 4,283,542 issued in 1981 to O'Lenick and Mayhew teaches the process technology used for the preparation of phosphobetaines. These compounds can be prepared by the reaction of a phosphate salt, one equivalent of epichlorohydrin and one equivalent of a tertiary amine.

U.S. Pat. No. 4,336,386 issued in 1982 to O'Lenick and Mayhew teaches the technology for the preparation of imidazoline derived phosphobetaines based upon phosphorous acid salts. These compounds can be prepared by the reaction of a phosphorous acid salt, one equivalent of epichlorohydrin and one equivalent of an imidazoline.

U.S. Pat. No. 4,503,002 which is related to U.S. Pat. No. 4,209,449 issued in 1985 to Mayhew and O'Lenick teach that phosphate quats can be prepared by the reaction of a phosphate salt, three equivalents of epichlorohydrin and three equivalents of a tertiary amine.

U.S. Pat. No. 5,070,171 issued to O'Lenick teaches that silicone phosphate esters can be prepared by phosphating internal (i.e. non-terminal) dimethicone copolyols. U.S. Pat. No. 5,091,493 issued to O'Lenick teaches that non-polymeric silicone phosphobetaines can be prepared using the phosphate esters of U.S. Pat. No. 5,070,171.

U.S. Pat. No. 5,149,765 to O'Lenick teaches that terminal dimethicone copolyols can be used to produce phosphates. These materials are the starting raw materials for preparation of the compounds of the present invention.

Despite the fact that there was significant patenting of phosphobetaine compounds based upon phosphoric acid salts, phosphorous acids salts, tertiary amines and imidazolines, and more recently silicone based phosphobetaines, the technology needed to make polymeric compounds was not available until the it was discovered that the terminal dimethicone copolyols could be used as starting materials for the preparation of polymeric silicone phospholipids. Terminal silicone phosphates are the basic raw material used for the preparation of polymeric silicone based phosphobetaines. This is due to the fact that the nature of these materials results in an unexpected film forming polymer which is non-occlusive and non-irritating. This suggests the use of these materials in barrier creams to protect the scalp from irritating processes like hair permanent waves and the relaxing of curly hair. The exact nature of the polymeric structure will become apparent.

THE INVENTION

Object of the Invention

It is the object of the present invention to provide a series of novel polymeric silicone phospholipids which are high foaming, low irritation to eyes and skin, have an inverse cloud point are substantive to the surface of a fibers and provide a polymer which is film forming upon drying.

Still another object of the present invention is to provide a series of polymeric silicone phospholipids which have differing solubilities in water and organic solvents. This is achieved by selection of the phosphated silicone polymer used as a raw material and the amine chosen for preparation of the polymeric phospholipid.

Application of the compounds of the invention can be from solvent, aqueous dispersion or solution, or applied neat in these processes.

The phosphated silicone polymers, suitable as raw materials, in a preferred embodiment, contain varying amounts of ethylene oxide, propylene oxide or butylene oxide or mixtures thereof. The presence of the oxide in the phosphated silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to skin, hair and fiber.

In another preferred embodiment a is in integer from 10 to 100; b is an integer from 10 to 100; and c is an integer from 5 to 20.

In still another preferred embodiment x, y and z are independently integers ranging from 1 to 10.

SUMMARY OF THE INVENTION

The present invention relates to a series of novel silicone phospholipid polymers. These compounds have a terminal phosphate functional group connected via a hydroxypropyl group to a amine group. The amine group typically will be a quaternized nitrogen. Hence the products are amphoterics having both an anionic and cationic group present on the same pendant group. The silicone polymer by virtue of this unique pendent group is highly foaming, non irritating to eyes and skin and deposits on fiber surfaces and form effective surface modifying finishes. The compounds of the present invention are therefore very well suited to applications in the personal care market.

The compounds of the present invention are prepared by the phosphation of terminal dimethicone copolyols, followed by reaction with epichlorohydrin (one or two mole equivalents) followed by reaction with amines. These amines can be primary secondary or tertiary.

One of the reasons why the product produced by the process of the present invention is polymeric is that the dimethicone copolyol has two terminal reactive groups. The phosphation reaction of the two groups gives mono and di phosphate ester. The di phosphate ester is a crosslinking group between dimethicone copolyols.

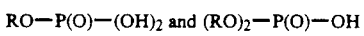

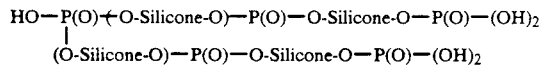

A second reason for the extended polymeric nature of the products of the present invention occurs as a consequence of the reaction with epichlorohydrin;

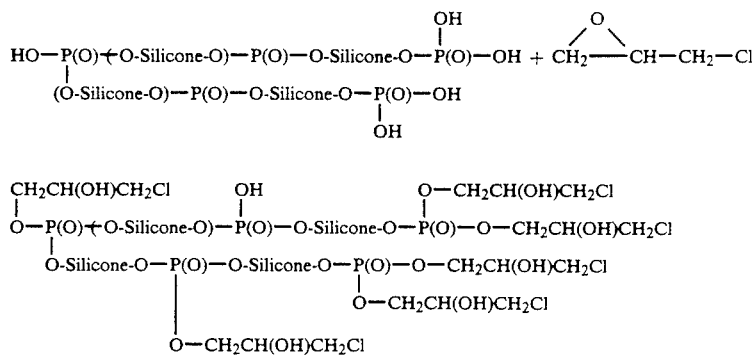

By reacting less on a molar basis of epichlorohydrin less of the phosphate groups are derivatized and the polymer's molecular weight is decreased.

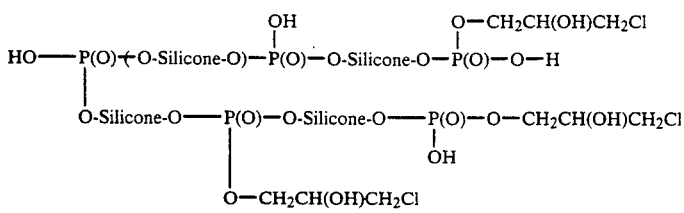

Thereby the polymeric structure can be regulated. Finally, the intermediate is reacted with an amine to give a phospholipid polymer.

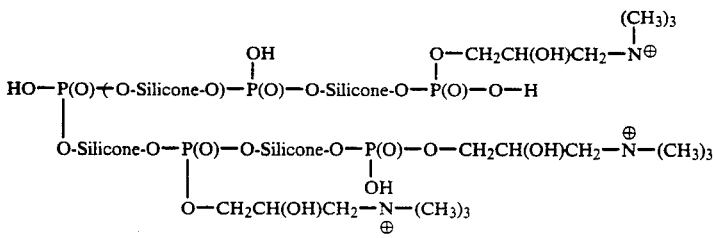

The compounds of the present invention unlike many other surface active agents which form micelles, unexpectedly form bilayers in aqueous solution by orientating themselves into the lowest energy configuration which happens to be sheets.

The compounds of this invention are prepared by reaction of (a) a terminal dimethicone copolyol conforming to the following structure;

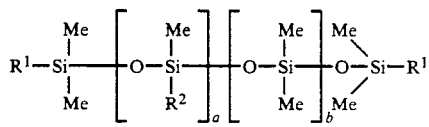

wherein;
Me is methyl;
a is an integer from 0 to 200;
b is an integer from 0 to 200;
$R^1$ is $-(CH_2)_3-O-(CH_2CH_2-O)_x-(CH_2CH(CH_3)-O)_y-(CH_2CH_2-O)_z-H$
$R^2$ is selected from $CH_3$ and phenyl;
x, y and z are integers and are independently selected from 0 to 20;
with (b) phosphating agent selected from the group consisting of polyphosphoric acid, phosphoric anhydride and phosphorus oxychloride said reaction to be conducted under anhydrous or nearly anhydrous conditions at a temperature of between 30 and 80 C.
followed by (c) neutralization of the phosphate with a base selected from the group consisting of NaOH, KOH, NH4OH, LiOH, in aqueous solution having a solid content of between 20 and 70% by weight to a pH of between 5 and 11
followed by (d) the condensation reaction with epichlorohydrin at a temperature of between 80 and 100 C. for four to ten hours
and subsequently (e) conducting an n-alkylation reaction with an amine selected from the group consisting of

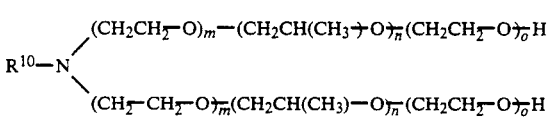

and

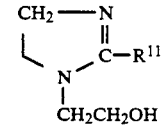

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are independently selected from lower alkyl having from one to three carbon atoms;
$R^{10}$ is alkyl having from 6 to 20 carbon atoms;
$R^{11}$ is alkyl having from 6 to 20 carbon atoms;
m, n, and o are independently integers each ranging from 0 to 20;
said n-alkylation reaction conducted at a temperature of between 50 and 80 C.

EXAMPLES

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856. These hydroxyl functional silicone compounds are subsequently phosphated.

Compounds suitable for use as reactants in the preparation of the compounds of the present invention conform to the following structure;

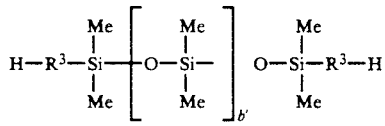

Me is methyl;
$R^3$ is $-(CH_2)_3-O-(CH_2CH_2-O)_x-(CH_2(CH_3)-CH-O)_y-(CH_2CH_2-O)_z-$
x, y and z are integers independently ranging from 0 to 20;
b' is an integer from 1 to 200.

These materials are available from Siltech Inc. Norcross Ga and are marketed under the Siltech T series tradename.

| Name | x | y | z | Molecular Weight |
|---|---|---|---|---|
| Siltech T 710 | 0 | 0 | 0 | 1,000 |
| Siltech T 706 | 5 | 1 | 0 | 6,000 |
| Siltech T 710 | 2 | 1 | 1 | 10,000 |
| Siltech T 750 | 10 | 5 | 10 | 50,000 |
| Siltech T 790 | 20 | 20 | 20 | 86,000 |

Phosphation

Phosphating Agents

Polyphosphoric Acid (PPA) is 115% phosphoric acid. When used as a phosphating agent in gives more mono ester than the phosphorus pentoxide. Phosphorus pentoxide is also called phosphoric anhydride. Phosphorus pentoxide is P2O5. It is more aggressive in phosphation and results in more diester.

The silicone phosphates of this invention can be prepared by reacting the terminal hydroxyl containing silicone polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence

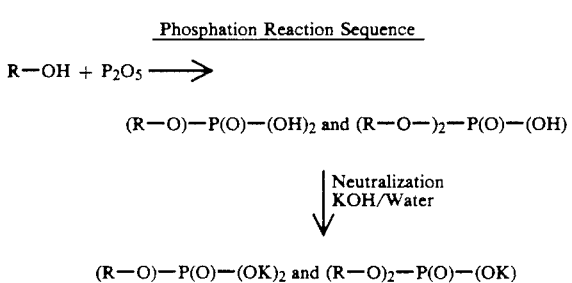

It will be understood by the above reaction that the product of phosphation, weather using polyphosphoric acid or phosphorus pentoxide give a mixture of mono and di ester. The following examples further illustrate the objects and advantages of this invention, though it should be understood that the various reactants and amounts thereof, reaction conditions, and other details are merely illustrative and should not be construed to unduly limit this invention.

PREFERRED EMBODIMENT

In one embodiment the tertiary amine is an tri alkyl amine conforming to the following structure;

$R^4$ is alkyl having from 1 to 20 carbon atoms;
$R^5$ is alkyl having from 1 to 20 carbon atoms;
$R^6$ is alkyl having from 1 to 20 carbon atoms.

In a preferred embodiment the tertiary amine reacted with the silicone hydroxypropyl intermediate is an N alkyl amido, N diakyl amine.

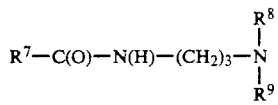

$R^7$ is alkyl having from 1 to 20 carbon atoms;
$R^8$ and $R^9$ are independently selected from lower alkyl having from one to three carbon atoms.

In an another preferred embodiment the tertiary amine reacted with the silicone hydroxypropyl intermediate is an imidazoline.

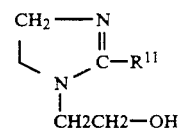

$R^{11}$ is alkyl having from 6 to 20 carbon atoms.

In still another preferred embodiment the tertiary amine reacted with the silicone hydroxypropyl intermediate is an bis alkoxyethyl alkyl amine conforming to the following structure;

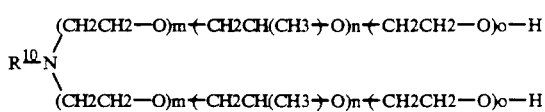

$R^{10}$ is alkyl having from 6 to 20 carbon atoms;
m, n, and o are independently integers each ranging from 0 to 20.

EXAMPLES

GENERAL PROCEDURE

The specified amount of hydroxy silicone compound (Siltech T series) is added to a suitable reaction vessel. The specified amount of either polyphosphoric acid or phosphorus pentoxide is charged to under good agitation over a 2 hr. period. The exothermic reaction raises the temperature of the mixture to about 70 C. After 1 hour slowly raise the temperature to 100 C. and hold 2-4 hours.

| Example | Hydroxy Silicone Name | Grams | Polyphosphoric Acid Grams |
|---|---|---|---|
| 1 | Siltech T 710 | 1,000 | 56.5 |
| 2 | Siltech T 706 | 6,000 | 56.5 |
| 3 | Siltech T 710 | 10,000 | 56.5 |
| 4 | Siltech T 750 | 50,000 | 56.5 |
| 5 | Siltech T 790 | 90,000 | 56.5 |

| | Phosphorus Pentoxide | | |
|---|---|---|---|
| Example | Hydroxy Silicone Name | Grams | Phosphorus Pentoxide Grams |
| 6 | Siltech T 710 | 1,000 | 36.0 |
| 7 | Siltech T 706 | 6,000 | 36.0 |
| 8 | Siltech T 710 | 10,000 | 36.0 |
| 9 | Siltech T 750 | 50,000 | 36.0 |
| 10 | Siltech T 790 | 90,000 | 36.0 |

The compounds of examples 1-10 are neutralized to pH 7 with 20% aqueous base. The following bases are used; NaOH, KOH, LiOH, NH4OH.

| Example | Phosphated Silicone Example | Base Type |
|---|---|---|
| 11 | 1 | KOH |
| 12 | 2 | NaOH |
| 13 | 3 | LiOH |
| 14 | 4 | NH4OH |
| 15 | 5 | KOH |
| 16 | 6 | NaOH |
| 17 | 7 | KOH |
| 18 | 8 | NaOH |
| 19 | 9 | KOH |
| 20 | 10 | NaOH |
| 21 | 1 | KOH |
| 22 | 2 | NaOH |
| 23 | 3 | KOH |
| 24 | 4 | NaOH |
| 25 | 5 | NaOH |

These materials are items of commerce available from Siltech Inc. Norcross, Ga.

The reactive intermediates are prepared by the reaction of one or two mole equivalents of epichlorohydrin with an equivalent of silicone phosphate ester. The mono adduct is made by reacting one equivalent each of epichlorohydrin and one equivalent of silicone phosphate. The diadduct is made by reacting two equivalents of epichlorohydrin and one equivalent of silicone phosphate.

INTERMEDIATE PREPARATION

Epichlorohydrin Reaction

As will be understood by the reaction sequences above there are two distinct reaction possibilities, namely the mono adduct and the diadduct. (Intermediate 1 and 2 respectively).

| | Mono Adducts Reactions Examples 26-40 | |
|---|---|---|
| Example | Phosphate Salt Example Number | Epichlorohydrin |
| 26 | 11 | 46.0 Grams |
| 27 | 12 | 46.0 Grams |
| 28 | 13 | 46.0 Grams |
| 29 | 14 | 46.0 Grams |
| 30 | 15 | 46.0 Grams |
| 31 | 16 | 46.0 Grams |
| 32 | 17 | 46.0 Grams |
| 33 | 18 | 46.0 Grams |
| 34 | 19 | 46.0 Grams |
| 35 | 20 | 46.0 Grams |
| 36 | 21 | 46.0 Grams |
| 37 | 22 | 46.0 Grams |
| 38 | 23 | 46.0 Grams |
| 39 | 24 | 46.0 Grams |
| 40 | 25 | 46.0 Grams |

EXAMPLES 41-55

Di Adduct Reactions

| Example | Phosphate Salt Example Number | Epichlorohydrin |
|---|---|---|
| 41 | 11 | 92.5 Grams |
| 42 | 12 | 92.5 Grams |
| 43 | 13 | 92.5 Grams |
| 44 | 14 | 92.5 Grams |
| 45 | 15 | 92.5 Grams |
| 46 | 16 | 92.5 Grams |
| 47 | 17 | 92.5 Grams |
| 48 | 18 | 92.5 Grams |
| 49 | 19 | 92.5 Grams |
| 50 | 20 | 92.5 Grams |
| 51 | 21 | 92.5 Grams |
| 52 | 22 | 92.5 Grams |
| 53 | 23 | 92.5 Grams |
| 54 | 24 | 92.5 Grams |
| 55 | 25 | 92.5 Grams |

Raw Material Amines

$R^4$ is alkyl having from 1 to 20 carbon atoms;
$R^5$ is alkyl having from 1 to 20 carbon atoms;
$R^6$ is alkyl having from 1 to 20 carbon atoms;

| Raw Material Example | $R^4$ | $R^5$ | $R^6$ | Molecular Weight |
|---|---|---|---|---|
| A | $CH_3$ | $C_{12}H_{25}$ | $CH_3$ | 213.0 |
| B | $C_2H_5$ | $C_6H_{13}$ | $C_2H_5$ | 143.0 |
| C | $CH_3$ | $C_8H_{17}$ | $CH_3$ | 143.0 |
| D | $CH_3$ | $C_{10}H_{21}$ | $CH_3$ | 171.0 |
| E | $CH_3$ | $C_{18}H_{37}$ | $CH_3$ | 283.0 |
| F | $CH_3$ | $C_{20}H_{41}$ | $CH_3$ | 311.0 |
| G | $C_6H_{13}$ | $C_6H_{13}$ | $CH_3$ | 185.0 |
| H | $CH_3$ | $C_{10}H_{21}$ | $C_{10}H_{21}$ | 297.0 |

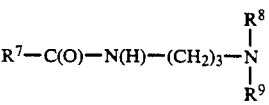

$R^7$ is alkyl having from 1 to 20 carbon atoms;
$R^8$ and $R^9$ are independently selected from lower alkyl having from one to three carbon atoms.

| Raw Material Example | $R^7$ | $R^8$ | $R^9$ | Molecular Weight |
|---|---|---|---|---|
| I | $C_7H_{15}$ | $CH_3$ | $CH_3$ | 129.0 |
| J | $C_{11}H_{23}$ | $CH_3$ | $CH_3$ | 185.0 |
| K | $C_{13}H_{27}$ | $CH_3$ | $CH_3$ | 213.0 |
| L | $C_{17}H_{35}$ | $CH_3$ | $CH_3$ | 269.0 |
| M | $C_{19}H_{39}$ | $C_2H_5$ | $C_2H_5$ | 325.0 |
| N | $C_6H_{13}$ | $C_2H_5$ | $C_2H_5$ | 143.0 |
| O | $C_{20}H_{21}$ | $C_2H_5$ | $C_2H_5$ | 319.0 |
| P | $C_{11}H_{23}$ | $C_2H_5$ | $C_2H_5$ | 213.0 |

$$R^{10}-N\begin{cases}(CH_2CH_2-O)_m(CH_2CH(CH_3)-O)_n(CH_2CH_2-O)_o H \\ (CH_2CH_2-O)_m(CH_2CH(CH_3)-O)_n(CH_2CH_2-O)_o H\end{cases}$$

$R^{10}$ is alkyl having from 6 to 20 carbon atoms;
m, n, and o are independently integers each ranging from 0 to 20.

| Raw Material Example | $R^{10}$ | m | n | o | Molecular Weight |
|---|---|---|---|---|---|
| Q | $C_6H_{13}$ | 20 | 20 | 20 | 3,039.0 |
| R | $C_{10}H_{21}$ | 0 | 0 | 0 | 155.0 |
| S | $C_{12}H_{25}$ | 5 | 1 | 5 | 682.0 |
| T | $C_{18}H_{37}$ | 0 | 10 | 0 | 857.0 |
| U | $C_{20}H_{21}$ | 5 | 1 | 10 | 994.0 |

$$\begin{array}{c}CH_2-N\\ \phantom{CH_2-}\|\\ \phantom{CH_2-N}C-R^{11}\\ N\\ |\\ CH_2CH_2OH\end{array}$$

$R^{11}$ is alkyl having from 6 to 20 carbon atoms.

| Raw Material Example | $R^{11}$ | Molecular Weight |
|---|---|---|
| V | $C_7H_{15}$ | 186.0 |
| W | $C_{11}H_{23}$ | 242.0 |
| X | $C_{17}H_{35}$ | 326.0 |
| Y | $C_{19}H_{40}$ | 355.0 |
| Z | $C_6H_{13}$ | 172.0 |

PHOSPHOLIPID PREPARATION

General Procedure

To the reaction product of epichlorohydrin with the aqueous, silicone phosphate salt prepared above in the specified example (examples 39-66) is added the specified number of grams of the specified amine reactant (Examples A-Z). Water is then added to make the solids 40%.

The resulting reaction mass is heated to 85-90 C and held for 4-6 hours. The pH is kept at or slightly above 7 by additions of small amounts of aqueous base, if needed. The batch clears and the desired phospholipid is obtained and used without purification. The reaction progress if followed by the percentage of inorganic chloride ion present. The reaction is complete when 97% of theoretical inorganic chloride ion has been generated.

Examples 56-93

| Example Number | Phospholipid Intermediate Example | Amine Reactant Example | Grams |
|---|---|---|---|
| 56 | 26 | A | 106.5 |
| 57 | 27 | B | 71.5 |
| 58 | 28 | C | 71.5 |
| 59 | 29 | D | 85.5 |
| 60 | 30 | E | 141.5 |
| 61 | 31 | F | 155.5 |
| 62 | 32 | G | 92.5 |
| 63 | 33 | H | 148.5 |
| 64 | 34 | I | 64.5 |
| 65 | 35 | J | 92.5 |
| 66 | 36 | K | 106.5 |
| 67 | 37 | L | 134.5 |
| 68 | 38 | M | 229.8 |
| 69 | 39 | N | 71.5 |
| 70 | 40 | O | 319.0 |
| 71 | 41 | P | 213.0 |
| 72 | 42 | Q | 3,039.0 |
| 73 | 43 | R | 155.0 |
| 74 | 44 | S | 682.0 |
| 75 | 45 | T | 857.0 |
| 76 | 46 | U | 994.0 |
| 77 | 47 | V | 186.0 |
| 78 | 48 | W | 242.0 |
| 79 | 49 | X | 326.0 |
| 80 | 50 | Y | 355.0 |
| 81 | 51 | Z | 172.0 |
| 82 | 52 | A | 213.0 |
| 83 | 53 | B | 143.0 |
| 84 | 54 | C | 143.0 |
| 85 | 55 | D | 171.0 |

APPLICATIONS EXAMPLES

Compounds of the present invention were found to provide to the hair conditioning, softening and antistatic properties. The compounds formed nococclusive films on the hair making the desirable properties listed above more permanent.

Compounds of the invention were found to be non-irritating to the skin and eye and were not orally toxic when tested in the LD-50 test.

What is claimed:

1. A polymeric silicone phospholipid prepared by;
(a) the phosphation reaction of a terminal dimethicone copolyol conforming to the following structure;

$$R^1-\underset{\underset{Me}{|}}{\overset{\overset{Me}{|}}{Si}}-\left[O-\underset{\underset{R^2}{|}}{\overset{\overset{Me}{|}}{Si}}\right]_a-\left[O-\underset{\underset{Me}{|}}{\overset{\overset{Me}{|}}{Si}}\right]_b-O-\underset{\underset{Me}{/}}{\overset{\overset{Me}{\backslash}}{Si}}-R^1$$

wherein;
Me is methyl;
a is an integer from 0 to 200;
b is an integer from 0 to 200;
$R^1$ is $-(CH_2)_3-O-(CH_2CH_2-O)_x-(CH_2CH(CH_3)-O)_y-(CH_2CH_2-O)_z-H$
$R^2$ is selected from the group consisting of $CH_3$ and phenyl;
x, y and z are integers and are independently selected from 0 to 20;
with
(b) a phosphating agent selected from the group consisting of polyphosphoric acid, phosphoric anhydride and phosphorus oxychloride said reaction to be conducted under anhydrous or nearly anhydrous conditions at a temperature of between 30 C. and 80 C.;

followed by;

(c) neutralization of the phosphate with a base selected from the group consisting of NaOH, KOH, NH$_4$OH, and LiOH, in aqueous solution having a solid content of between 20 and 70% by weight to a pH of between 5 and 11;

followed by;

(d) a condensation reaction with epichlorohydrin at a temperature of between 80 and 100 C. for four to ten hours;

and subsequently;

(e) conducting an n-alkylation reaction with an amine selected from the group consisting of;

$$\begin{array}{c} R^6 \\ | \\ N-R^4 \\ | \\ R^5 \end{array}$$

$$R^7-C(O)-N(H)-(CH_2)_3-\underset{\underset{R^9}{|}}{\overset{\overset{R^8}{|}}{N}};$$

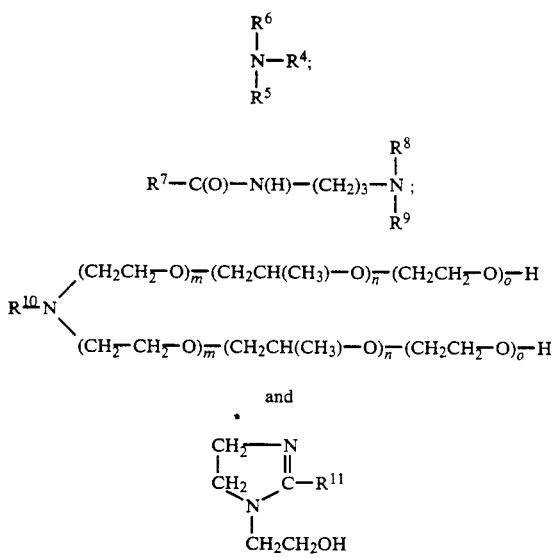

and

CH$_2$CH$_2$OH

R$^4$ is alkyl having from 1 to 20 carbon atoms;
R$^5$ is alkyl having from 1 to 20 carbon atoms;
R$^6$ is alkyl having from 1 to 20 carbon atoms;
R$^7$ is alkyl having from 1 to 20 carbon atoms;
R$^8$ and R$^9$ are independently selected from lower alkyl having from one to three carbon atoms;
R$^{10}$ is alkyl having from 6 to 20 carbon atoms;
R$^{11}$ is alkyl having from 6 to 20 carbon atoms;
m, n, and o are independently integers each ranging from 0 to 20; said n-alkylation reaction conducted at a temperature of between 50 and 80 C.

2. A polymeric silicone phospholipid of claim 1 wherein said amine conforms to the following structure;

$$\begin{array}{c} R^6 \\ | \\ N-R^4 \\ | \\ R^5 \end{array}$$

R$^4$ is alkyl having from 1 to 20 carbon atoms;
R$^5$ is alkyl having from 1 to 20 carbon atoms;
R$^6$ is alkyl having from 1 to 20 carbon atoms.

3. A polymeric silicone phospholipid of claim 1 wherein said amine conforms to the following structure;

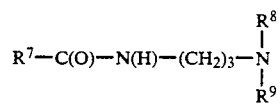

R$^7$ is alkyl having from 1 to 20 carbon atoms;
R$^8$ and R$^9$ are independently selected from lower alkyl having from one to three carbon atoms.

4. A polymeric silicone phospholipid of claim 1 wherein said amine conforms to the following structure;

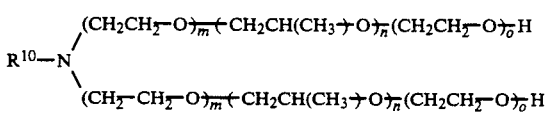

R$^{10}$ is alkyl having from 6 to 20 carbon atoms;
m, n, and o are independently integers each ranging from 0 to 20.

5. A polymeric silicone phospholipid of claim 1 wherein said amine conforms to the following structure;

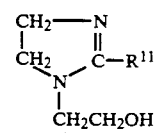
CH$_2$CH$_2$OH

R$^{11}$ is alkyl having from 6 to 20 carbon atoms.

6. A polymeric silicone phospholipid of claim 1 wherein x, y and z are all zero.

7. A polymeric silicone phospholipid of claim 1 wherein R$^2$ is methyl.

8. A polymeric silicone phospholipid of claim 1 wherein R$^2$ is phenyl.

9. A process for the preparation of polymeric silicone phospholipid which comprises;

(a) the phosphation reaction of a terminal dimethicone copolyol conforming to the following structure;

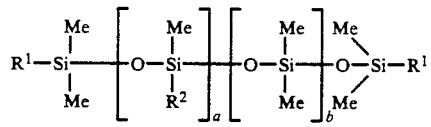

wherein;
Me is methyl;
a is an integer from 0 to 200;
b is an integer from 0 to 200;
R$^1$ is —(CH$_2$)$_3$—O—(CH$_2$CH$_2$—O)$_x$-—(CH$_2$CH(CH$_3$)—O)$_y$—(CH$_2$CH$_2$—O)$_z$—H
R$^2$ is selected from the group consisting of CH$_3$ and phenyl;
x, y and z are integers and are independently selected from 0 to 20;

with (b) a phosphating agent selected from the group consisting of polyphosphoric acid, phosphoric anhydride and phosphorus oxychloride said reaction to be conducted under anhydrous or nearly anhydrous conditions at a temperature of between 30 C. and 80 C.;

followed by;

(c) neutralization of the phosphate with a base selected from the group consisting of NaOH, KOH, NH₄OH, and LiOH, in aqueous solution having a solid content of between 20 and 70% by weight to a pH of between 5 and 11;

followed by;

(d) a condensation reaction with epichlorohydrin at a temperature of between 80 and 100 C. for four to ten hours;

and subsequently;

(e) conducting an n-alkylation reaction with an amine selected from the group consisting of;

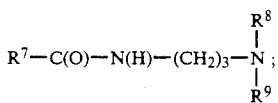

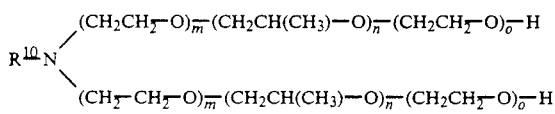

and

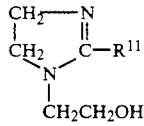

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are independently selected from lower alkyl having from one to three carbon atoms;
$R^{10}$ is alkyl having from 6 to 20 carbon atoms;
$R^{11}$ is alkyl having from 6 to 20 carbon atoms;

m, n, and o are independently integers each ranging from 0 to 20;
said n-alkylation reaction conducted at a temperature of between 50 and 80 C.

10. A process of claim 9 wherein said amine conforms to the following structure;

$R^4$ is alkyl having from 1 to 20 carbon atoms;
$R^5$ is alkyl having from 1 to 20 carbon atoms;
$R^6$ is alkyl having from 1 to 20 carbon atoms.

11. A process of claim 9 wherein said amine conforms to the following structure;

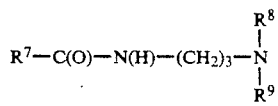

$R^7$ is alkyl having from 1 to 20 carbon atoms;
$R^8$ and $R^9$ are independently selected from lower alkyl having from one to three carbon atoms.

12. A process of claim 9 wherein said amine conforms to the following structure;

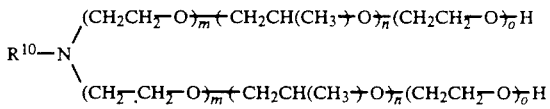

$R^{10}$ is alkyl having from 6 to 20 carbon atoms;
m, n, and o are independently integers each ranging from 0 to 20.

13. A process of claim 9 wherein said amine conforms to the following structure;

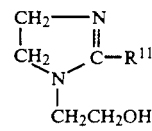

$R^{11}$ is alkyl having from 6 to 20 carbon atoms.

* * * * *